(12) United States Patent
Holce et al.

(10) Patent No.: US 8,861,156 B1
(45) Date of Patent: Oct. 14, 2014

(54) STATUS PROVIDING STARTER APPARATUS, SYSTEM, AND/OR METHOD

(76) Inventors: Kent Jeffrey Holce, Portland, OR (US); Andre Pierre Perra, Portland, OR (US); Roger Steven Cota, Ridgefield, WA (US)

( * ) Notice: Subject to any disclaimer, the term of this patent is extended or adjusted under 35 U.S.C. 154(b) by 0 days.

(21) Appl. No.: 13/450,461

(22) Filed: Apr. 18, 2012

Related U.S. Application Data

(63) Continuation-in-part of application No. 11/784,117, filed on Apr. 4, 2007, now Pat. No. 8,300,372.

(60) Provisional application No. 61/517,436, filed on Apr. 18, 2011, provisional application No. 60/789,277, filed on Apr. 4, 2006.

(51) Int. Cl.
*H02H 3/00* (2006.01)
*H02H 9/02* (2006.01)

(52) U.S. Cl.
USPC ............................................. 361/79; 361/93.1

(58) Field of Classification Search
USPC .................................................. 361/79, 93.1
See application file for complete search history.

(56) References Cited

U.S. PATENT DOCUMENTS

| | | | |
|---|---|---|---|
| 4,833,628 A | 5/1989 | Curran, Jr. | |
| 4,894,588 A | 1/1990 | Stack | |
| 4,914,386 A | 4/1990 | Zocholl | |
| 5,428,495 A | 6/1995 | Murphy et al. | |
| 5,436,784 A | 7/1995 | Schweitzer, III et al. | |
| 5,539,651 A | 7/1996 | Zabar et al. | |
| 5,589,809 A | 12/1996 | Kogawa et al. | |
| 5,610,579 A * | 3/1997 | Early et al. | 340/517 |
| 5,715,129 A | 2/1998 | Innes | |
| 5,822,164 A * | 10/1998 | Graf | 361/23 |
| 5,864,458 A | 1/1999 | Duffy et al. | |
| 6,008,618 A | 12/1999 | Bose et al. | |
| 6,313,727 B1 | 11/2001 | Gabriel | |
| 6,611,411 B2 | 8/2003 | Williams et al. | |
| 6,611,785 B1 | 8/2003 | Yamanaka et al. | |
| 6,731,193 B2 | 5/2004 | Meier et al. | |
| 6,813,123 B2 | 11/2004 | Pihl | |
| 6,822,547 B2 | 11/2004 | Saito et al. | |
| 6,856,515 B2 | 2/2005 | Holce et al. | |
| 6,950,292 B2 | 9/2005 | Holce et al. | |
| 7,123,457 B2 | 10/2006 | Schweitzer, III et al. | |
| 7,161,778 B2 | 1/2007 | Zocholl | |
| 7,345,488 B2 | 3/2008 | Fischer | |
| 7,532,956 B1 | 5/2009 | Pelaez, Jr. et al. | |
| 2004/0109267 A1* | 6/2004 | Habetler | 361/23 |
| 2004/0178875 A1 | 9/2004 | Saito | |
| 2004/0252421 A1* | 12/2004 | Knox et al. | 361/23 |
| 2005/0224323 A1* | 10/2005 | Bortolloni et al. | 200/50.05 |

(Continued)

*Primary Examiner* — Scott Bauer
(74) *Attorney, Agent, or Firm* — Northwest IP Law Group, LLC

(57) ABSTRACT

A method, system, and/or apparatus is described for controllably providing operating power to, and indicating proper operating status of, a load. Novel functionality can be provided via discrete electronic components or components can be integrated into a unified enclosure as a starter apparatus. Operation can be based, at least in part, on an operating mode selected via a user interface. An electronic overload relay or overload circuit interconnected with a control board assembly and a contactor relay can sense one or more aspects of the operating power supplied to the load and the control board assembly can operate one or more relays to indicate operating status of the load and control the load in response to various manual or remote automation system inputs.

34 Claims, 17 Drawing Sheets

(56) References Cited

U.S. PATENT DOCUMENTS

| | | |
|---|---|---|
| 2005/0253544 A1 | 11/2005 | Fitzgbbon et al. |
| 2005/0270707 A1 | 12/2005 | Plemmons et al. |
| 2008/0048640 A1 | 2/2008 | Hull et al. |
| 2008/0208491 A1 | 8/2008 | Burlak et al. |

* cited by examiner

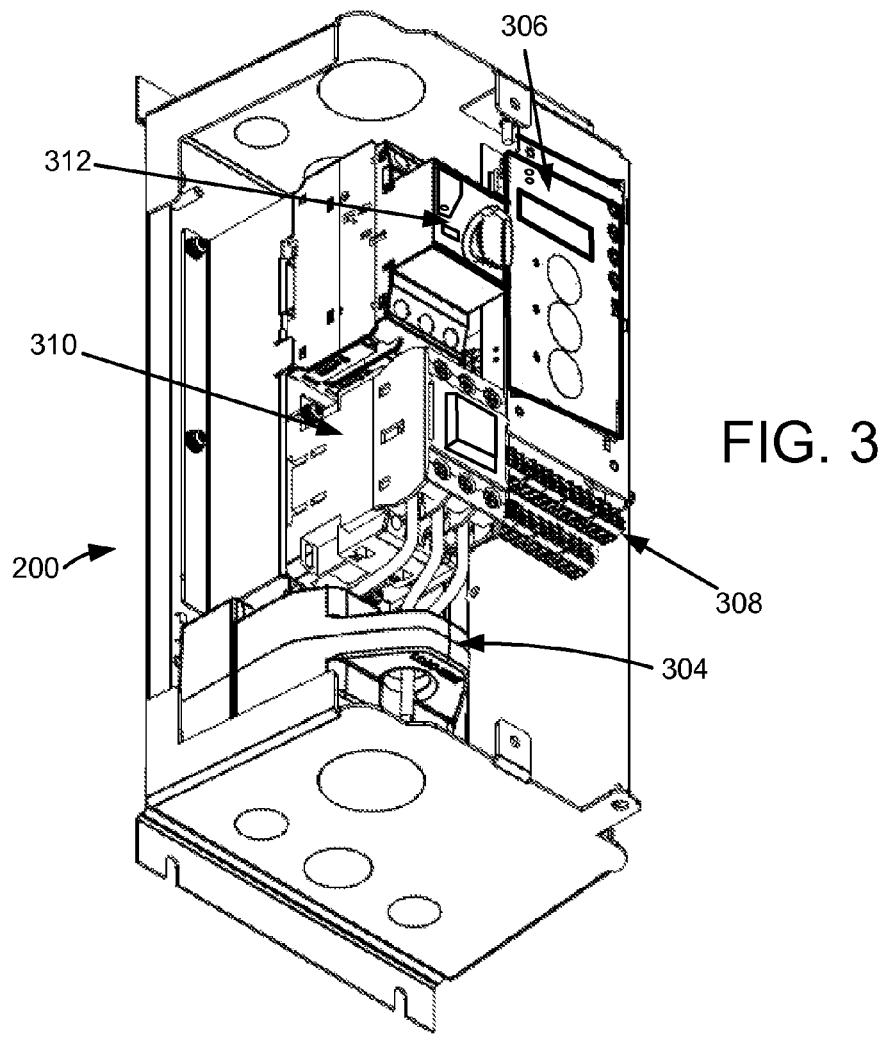
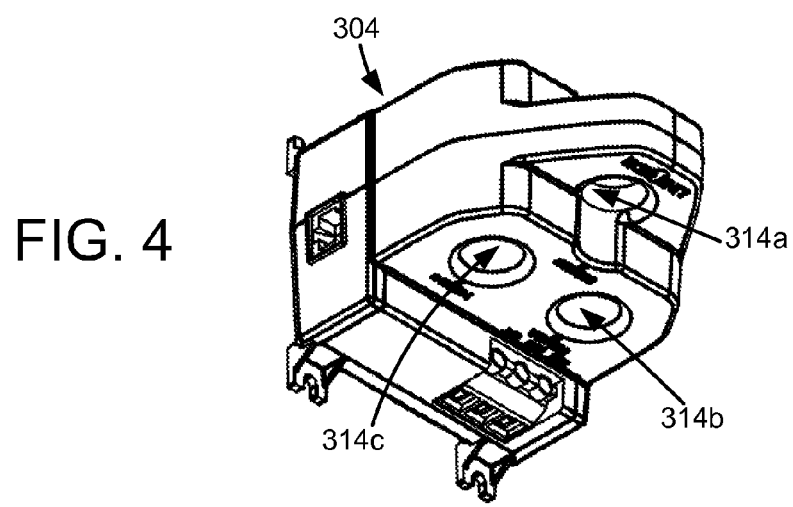

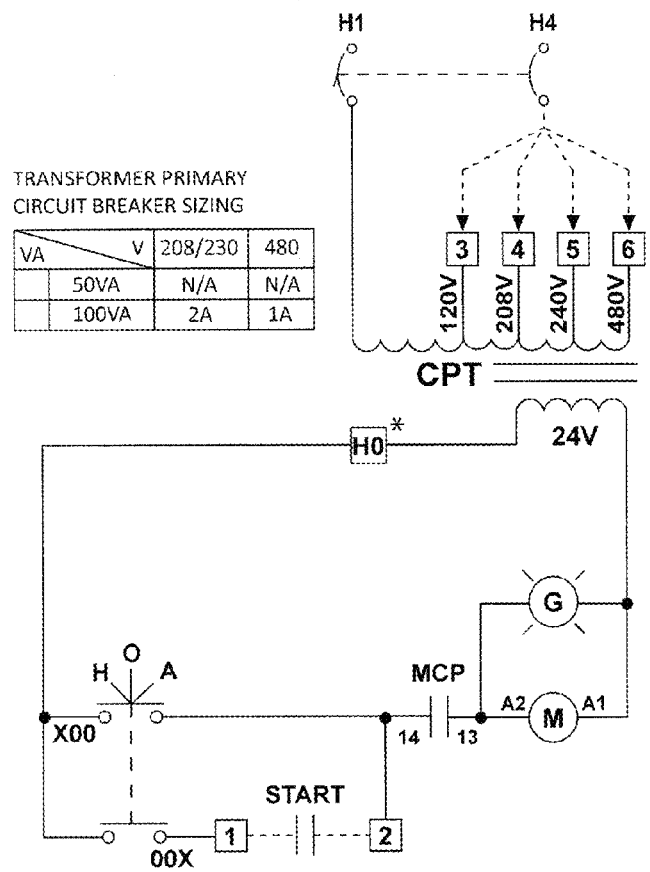
FIG. 5C
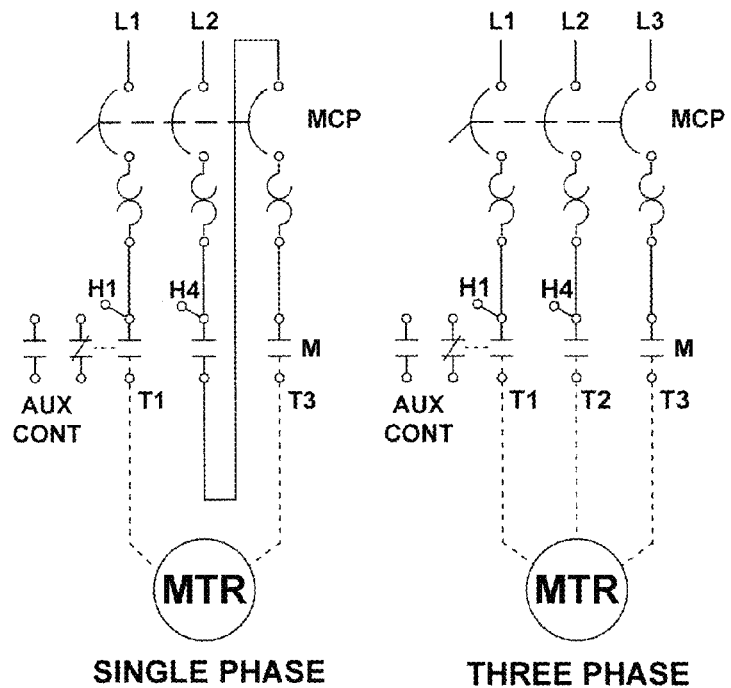
* H0 Terminal applies to 3R or 4/12 enclosed configurations only

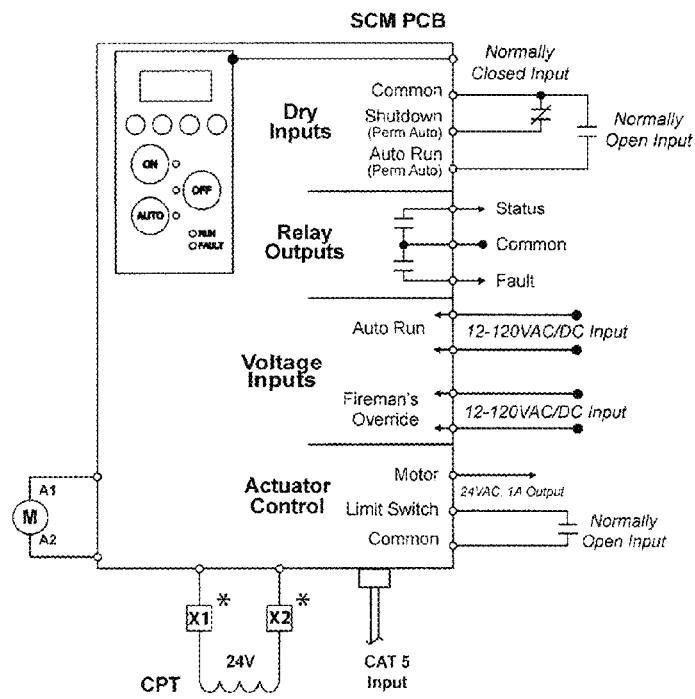
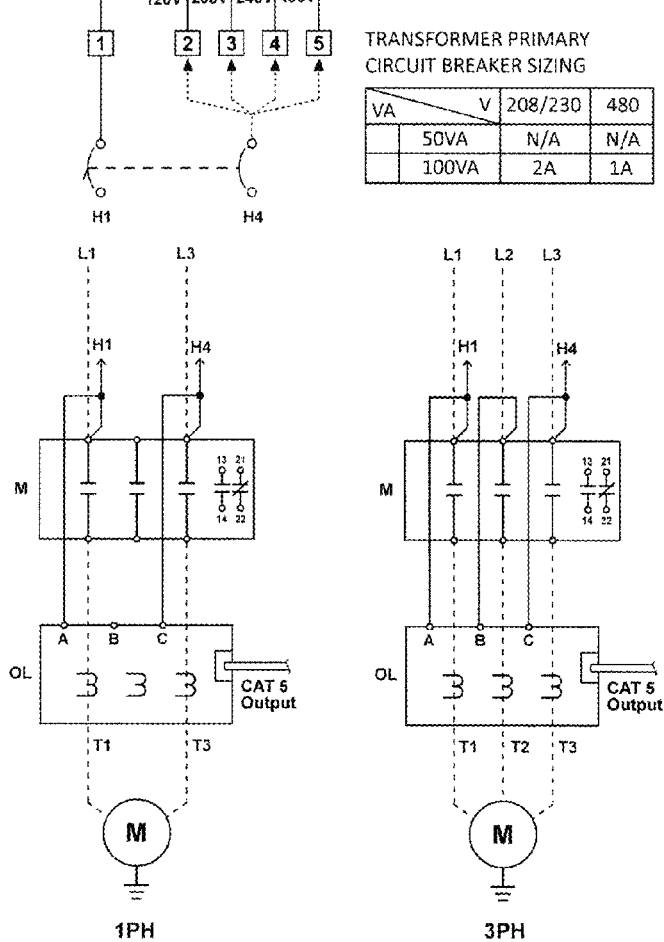
FIG. 6B
*X1 and X2 Terminals do not apply for Type 1 enclosed configurations

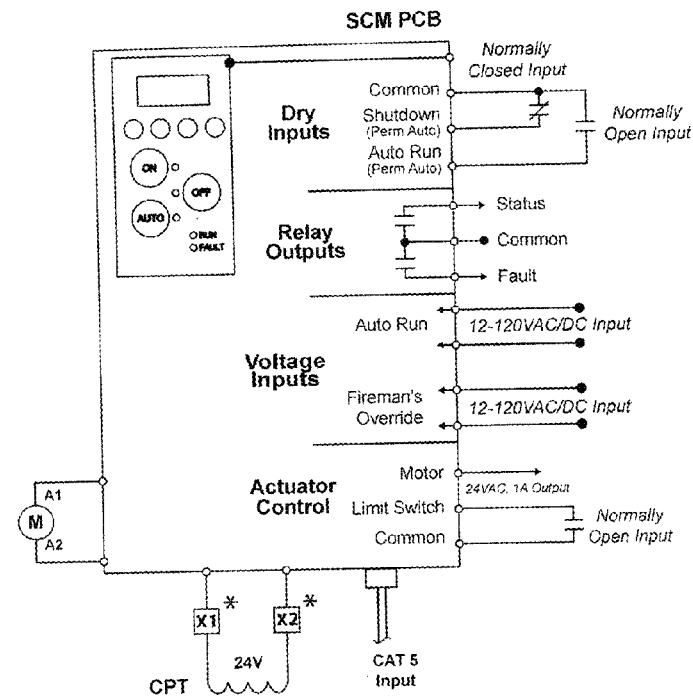
FIG. 6C
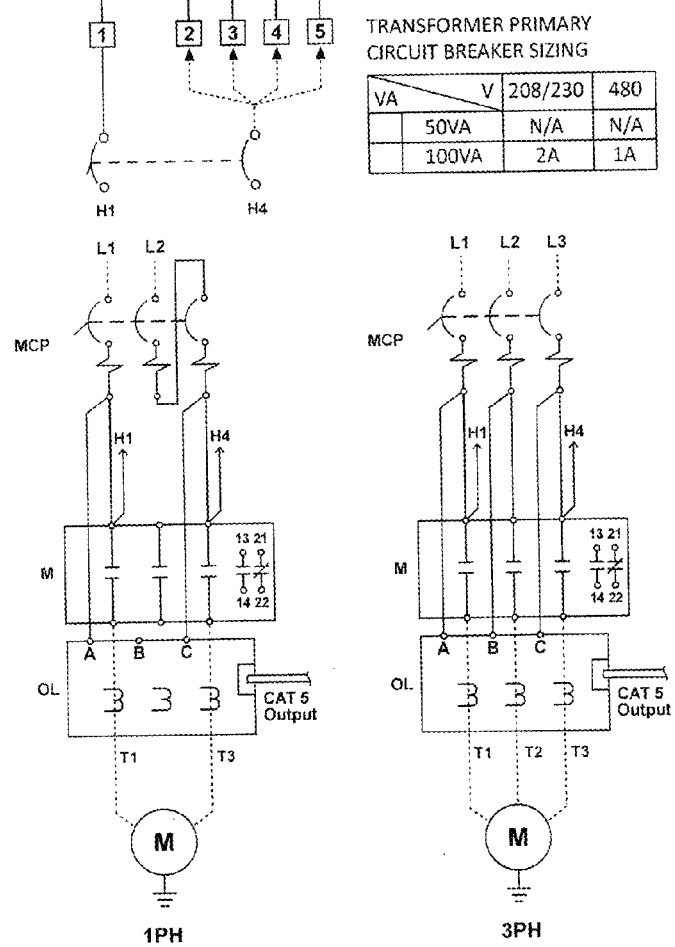

All dimensions in inches

STATUS PROVIDING STARTER APPARATUS, SYSTEM, AND/OR METHOD

RELATED APPLICATIONS

This application is a nonprovisional of, and claims the benefit of priority from, U.S. Provisional Patent Application No. 61/517,436, filed Apr. 18, 2011, and is a continuation-in-part of U.S. Nonprovisional patent application Ser. No. 11/784,117, filed Apr. 4, 2007, now U.S. Pat. No. 8,300,372, which in turn is a nonprovisional of and claims priority from U.S. Provisional Patent Application No. 60/789,277, filed Apr. 4, 2006, each of which is hereby incorporated by reference in its entirety.

COPYRIGHT NOTICE

© 2012 Cerus Industrial Corporation. A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR §1.71 (d), (e).

TECHNICAL FIELD

The present application is directed to the field of starters for loads such as motors driving fans, pumps, or other equipment, as well as lighting, etc., and, in particular, directed to starters, starting circuits, and related electronics capable of operating within a building, industrial, or other automation system.

BACKGROUND

To protect an electric motor or other electrical device from damage due to an undesirable operating condition, such as an overload, under load, etc. industrial control systems can employ, as a standard power distribution method, a method of combining a relay, such as an overload relay, which is typically in the form of a thermal overload relay or an electronic overload relay, along with a contactor relay, such as an electromagnetic contactor, connected to a power circuit supplying operating power to the electric motor. In an overload operation, the electromagnetic contactor is allowed to cut off current to stop the electric motor, thus preventing potentially dangerous excessive current from damaging the motor, conductors, or other equipment.

Presently available thermal overload relays utilize heater and detector elements suitable for measuring only small amperage increments per each heater and detector element. Thermal overload relays typically have a small current adjustment range of 1.5:1, meaning the maximum setting is 1.5 times the lower setting. However, there are a wide variety of industrial control systems encompassing numerous current ranges that an overload relay may have to accommodate. This requires numerous sizes to be available in order to practically address common loads. For example, a typical IEC style contactor frame size is 45 mm wide and contactors switching up to 22 A are commonly manufactured in this single frame size. For this same 45 mm frame size, over 15 different thermal overload sizes are required (e.g., 0.1-0.16 A, 0.16-0.25 A, etc up to 16-22 A) to accommodate motor protective loads up to 22 A. The sheer number of thermal overload combinations is costly to inventory and can result in incorrectly ordered and/or incorrectly sized overloads being applied.

Compared to thermal overloads, electronic overloads are capable of measuring wider current ranges by utilizing current transformers. However, current transformers are subject to saturation, therefore accuracy degrades as the magnetics of the transformer saturate with increased current. This effectively limits the applicable current ranges. The current state of the art adjustment range of presently available electronic overload relays is typically limited to approximately 3.2 to 1, meaning the maximum setting is 3.2 times the lower setting. However, this still requires numerous overload sizes to be available to address the loads covered by a typical IEC 45 mm frame size contactor. In this frame size, up to 22 A is typically switched, yet over 5 different overload sizes can still be required (e.g., 0.1-0.32 A, 0.32-1.0 A, 1.0-2.9 A, 1.6-5.0 A, 3.7-12 A). Again, the sheer number of overload combinations is costly to inventory and can result in incorrectly ordered and/or incorrectly sized overloads being applied.

Electronic overloads require power for their circuitry, which poses certain challenges, as the readily available line voltage being switched is typically far in excess of the electronic overload power supply requirements (e.g. 480 VAC line voltage vs. 24 VAC electronic overload power required). With traditional electronic overloads, this necessitates the use of an external power supply. Certain models, such as Sprecher and Shuh CEP7, induce their power from the conductor being monitored using current transformers. However, this technique has limitations, as the current transformers are also used for measurement and subject to limited current measurement range.

U.S. Pat. No. 5,715,129 ("Innes"), issued Feb. 3, 1998, teaches an electronic overload relay having a power supply in series with the normally closed contact of the overload relay. The power supply is an integral element of the electronic overload relay in Innes. The relay is connectable to an electromagnetic contactor in keeping with conventions of thermal overload relays wherein the contactor coil is connected in series with the normally closed contact of the relay, and therefore also in series with the power supply to provide power for the overload relay when power is supplied to the contactor coil. A processor in the electronic overload relay is instructed to assume a sleep (low power consumption) mode during the closing of the contactor. A semiconductor switch in the power supply is operated by the processor in low voltage coil applications to directly connect the coil of the contactor in shunt of the power supply for the relay while the contactor closes. However, while providing a technique to power the electronic overload circuitry, the device in Innes is dependent on contactor coil voltage being in a suitable range for direct input to the electronics circuitry (e.g., 24 VAC). In practice, contactors are often controlled through a push button or actuated using line voltages through the contactor coil. In these instances, utilizing coil voltages to power the contactor would not be feasible due to high line voltages (e.g. 480 VAC) incompatible with the device.

U.S. Pat. No. 5,589,809 ("Kogawa et al."), issued Dec. 31, 1996, relates to an adjusting dial of a thermal overload relay for adjusting a working current of the thermal overload relay, and, more specifically, to a structure of the relay which can prevent an adjusting dial previously set from being mis-readjusted. However, Kogawa et al. still requires an initial manual setting of the thermal overload for the proper load rating, which is a labor intensive process and potentially subject to error.

Both thermal and electronic overloads require field calibration in order to establish the set-point of the normal full load amperage of the load monitored. Field calibration is a manual task, and as such, can be expensive and prone to human error. As a result, equipment may not be properly protected, nuisance trips may result, and life safety issues may arise should an overload be improperly sized or adjusted. Further, improperly sized overloads, or contactors, can require frustrating, costly, and time-consuming extra labor when installers are required to return to an installation site to switch out improperly sized or rated equipment.

SUMMARY

Apparatuses, systems, and/or methods are described herein for providing automated and/or manually operated protection and/or control of electrical motors and/or other electrical devices. Embodiments as disclosed in the present application can substantially satisfy many of the needs unfulfilled by mechanisms previously available for the protection and control of electrical devices. One or more present embodiments can provide for wide-range current measurement, self-calibration, and wide-range line-powered electronics to provide application flexibility and/or reliable, cost-effective installation.

Traditional electrical switching devices providing starter functionality for loads such as motors, HVAC fans, lighting, pumps, etc., generally include an electromagnetic contactor with an overload relay (either thermal or electronic). Novel and improved functionality, as disclosed herein, can be provided via discrete electronic components or components that can be manufactured and integrated into a unified enclosure as a starter apparatus for controllably providing operating power to, and indicating proper operating status of, a load. Operation can be based, at least in part, on an operating mode selected via a provided user interface. An electronic overload relay or overload circuit interconnected with a control board assembly and a contactor relay can sense one or more aspects of the operating power supplied to the load and the control board assembly and can operate one or more relays to indicate operating status of the load, provide energy management and/or metering functionality, and/or control operation of the load and/or related and/or interconnected auxiliary devices in response to manual and/or remote automation system inputs, as but a few examples of advantageous functionality enabled and/or facilitated by embodiments as described herein.

One present embodiment can encompass an electrical measurement and/or control apparatus substantially suitable for motor protection and/or industrial control that can measure current ranges that are substantially wide in comparison to those measured by traditional thermal or electronic overload relays. The substantially broader applicability achieved by implementing such an embodiment can substantially reduce the number and/or type of overload relays (or other applicable electrical device protection mechanisms) required to be stored in inventory in order to accommodate the various amperage ranges that may be encountered in various control systems. This can allow for a substantial reduction in the amount of costly inventory that has to be maintained.

One or more embodiments consistent with the present application can implement auto-calibrating functionality that can prove advantageous in addressing overload, under load, and/or other undesirable operating conditions and/or parameters that may be encountered in industrial control systems, such as power distribution systems, as but one example. One embodiment can encompass an electrical measurement and control apparatus that can discern load types and levels and set motor set points, over current trip points, or other appropriate protection and/or control parameters substantially automatically. In addition, or in the alternative, an embodiment can encompass an electrical measurement and/or control apparatus that can discern load types and applicable operating characteristics (such as full load amperage, as but one example) either manually or automatically, and set motor under load set points substantially automatically (e.g. to establish proof of flow conditions for fans and pumps and/or correspondingly indicate the run status, as but one example). Such embodiments can substantially reduce the need for manual field calibration, which can, at least in part, reduce labor requirements for installation and increase accuracy and reliability of installation.

In an alternative embodiment, an overload relay or other control device can be provided which can accommodate a range of current, voltage, and/or other parameter values, but also accept at least some amount of manual input to fine tune, filter, or otherwise aid in the identification and/or selection of overload set points and/or other operating ranges and/or parameters. Such an alternative embodiment can be offered based, at least in part, on design choice considerations, and/or it can be offered based, at least in part, on economic considerations, such as if a manual-input device can be manufactured more economically than devices solely enabling fully-automatic calibration. By allowing variable accommodation of a wide range of potential input values, such as voltage or current, such an embodiment can offer functionality in a variety of applications or system environments. The embodiment can substantially provide this range of applicable functionality in a single device, rather than requiring a separate, statically set device to be purchased and inventoried for each potentially desirable value.

One embodiment consistent with the present application can encompass an electrical measurement and/or control apparatus that can be line powered over a wide range of currents and voltages, substantially reducing the need for external power supplies or dependence on costly current transformers. In addition, or in the alternative, an embodiment can encompass an electrical measurement and/or control apparatus that can be line powered to enable sensing of voltage, in addition to current in a conducting wire, to allow for substantially true power measurement and a resulting substantially superior load level detection.

While, for convenience, manufacturing efficiencies, cost savings, and/or other reasons, embodiments as disclosed herein can be provided as one or more electrical measurement and/or control apparatuses that can be integrated into a substantially unitary housing along with a contactor to encompass a starter for electronic motors and other electronic devices, alternative embodiments of control board assemblies as disclosed herein can be provided to work with a third-party manufacturer's contactor and/or current sensors to provide at least portions of the presently described functionality in retrofit or legacy system installations.

Additional aspects and advantages of the present application will be apparent from the following detailed description of preferred embodiments, which proceeds with reference to the accompanying drawings.

BRIEF DESCRIPTION OF THE DRAWINGS

FIG. 3 illustrates the motor starter of FIG. 2 with an enclosure cover removed to illustrate internal components.

FIG. 4 depicts one embodiment of a meter based having integrated current transformers.

FIG. 5B-5C schematically illustrate alternative embodiments of the schematically illustrated wiring diagram of FIG. 5A.

FIG. 6B-6C schematically illustrate alternative embodiments of the schematically illustrated wiring diagram of FIG. 6A.

DETAILED DESCRIPTION

Figure 1:
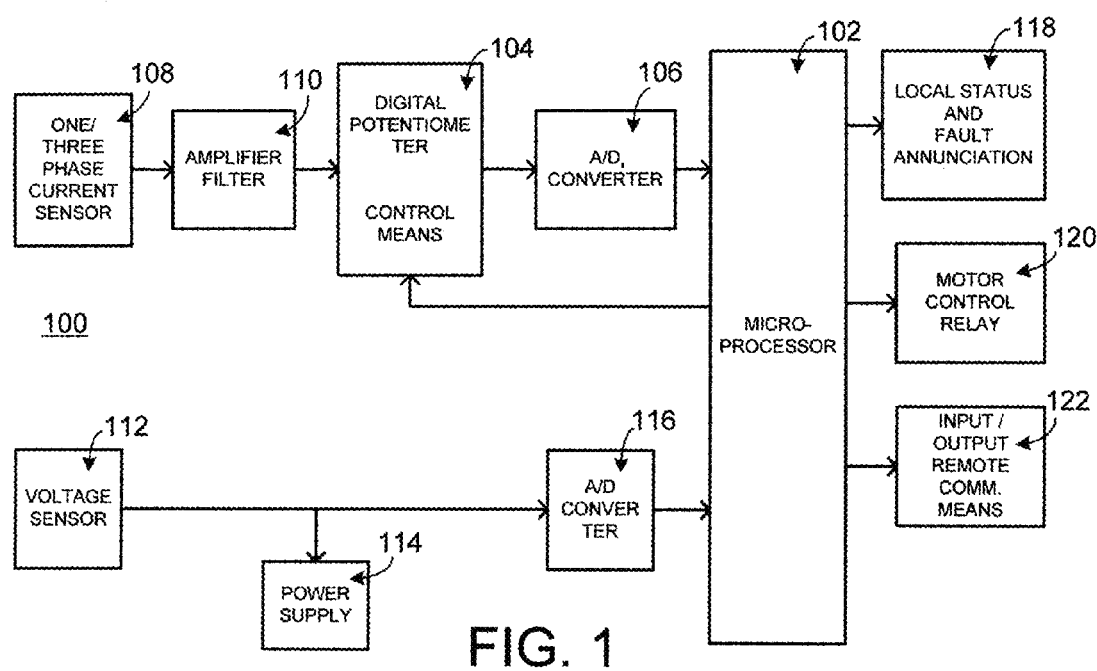
FIG. 1 illustrates one embodiment of an industrial control system for the automatic protection and/or control of electrical motors and/or other electrical devices.

As disclosed in the present application, one or more embodiments can be provided encompassing methods, apparatuses, and/or systems that can provide starting functionality and manual and/or substantially automated protection and/or control of electrical motors and/or other electrical devices in power distribution and/or other industrial control systems. FIG. 1 illustrates one embodiment of an industrial control system consistent provided for illustrative purposes, and not by way of limitation. With reference to the particular system illustrated in FIG. 1, the control system 100 includes a microprocessor 102 that receives signals from a current sensor 108 through an amplifier/filter 110 to a digital potentiometer 104 (or other prescaler and control mechanism), via an analog to digital converter 106. Also, microprocessor 102 can employ a voltage sensor 112 to measure line voltage to represent true power, and as a power supply 114 for the microprocessor 102. The microprocessor can then generate annunciation signals 118, control signals 120, and/or communication signals 122. Those skilled in the relevant arts will readily appreciate that additions, deletions, and/or modifications can be made to the system illustrated in FIG. 1, and/or the components illustrated therein, without diminishing the applicability of, or departing from the scope of, the present application.

To help optimize building performance, provide intelligent energy metering and management, and offer, at least in part, simplified installation and robust operating control options, one or more starter embodiments, as disclosed in more detail below, can be provide significant improvements over traditional starter apparatuses.

For improved building optimization, present starter embodiments can provide integration with automation systems. Both manual and automatic operation can be accommodated for ease of use and flexibility. Combining starter operation with on-site controls can result in extended equipment life and saved energy. Present starters can even be provided for small single phase motors previously plagued by prohibitive cost to control. Such starters can include integrated fireman's override functionality (e.g., for purging smoke in case of fire, etc.). They can also be sophisticated enough to automatically detect belt loss (either on a true power-loss or current-loss basis for the load).

Installation can also be substantially simplified with present starter embodiments. Integrated components can provide the desired functionality while being assembled in a unified enclosure so as to substantially eliminate or reduce the need for interposing relays and current sensors. Additionally incorporating wide-range overloads helps minimize callbacks due to miss-sized overloads being employed.

Starter embodiments consistent with the present application can also greatly facilitate measurement and management of energy. This can help achieve LEED green building points and manage consumption by monitoring loads with built in ANSI grade metering—providing not only kWh, but voltage, kVar, as well as other desired and/or beneficial attributes. Additionally, starter embodiments can offer automation system compatibility from pulse analog to BACnet communication options for plug and play interoperability, as but two examples. Of course, other automation system and/or communication protocols could equally be supported by present embodiments. Providing data stream and network direct control at a substantially fast transmission baud rate can reduce operational cost and facilitate easy commissioning.

One or more starter embodiments consistent with the present application can also substantially bolster system reliability. Incorporated electronic overload protection devices can help prevent motor damage and ensuring downtime or replacement cost. Present embodiments can also track restart activity and protect against rapid cycling. Also, as a matter of convenience and to improve installation effectiveness/accuracy, starters that are ordered or shipped in bulk or in large groupings can be provided with customizable job tags or similar labeling for improved identification and installation location guidance.

For convenience, reliability, or other reasons, one or more aspects and/or functions of starter embodiments as disclosed herein can be offered by electronic components that can be combined into a single, unitary starter enclosure. Such enclosure can encompass a standard starter, or a combination starter with a disconnect and/or motor circuit protection option.

Figure 2:
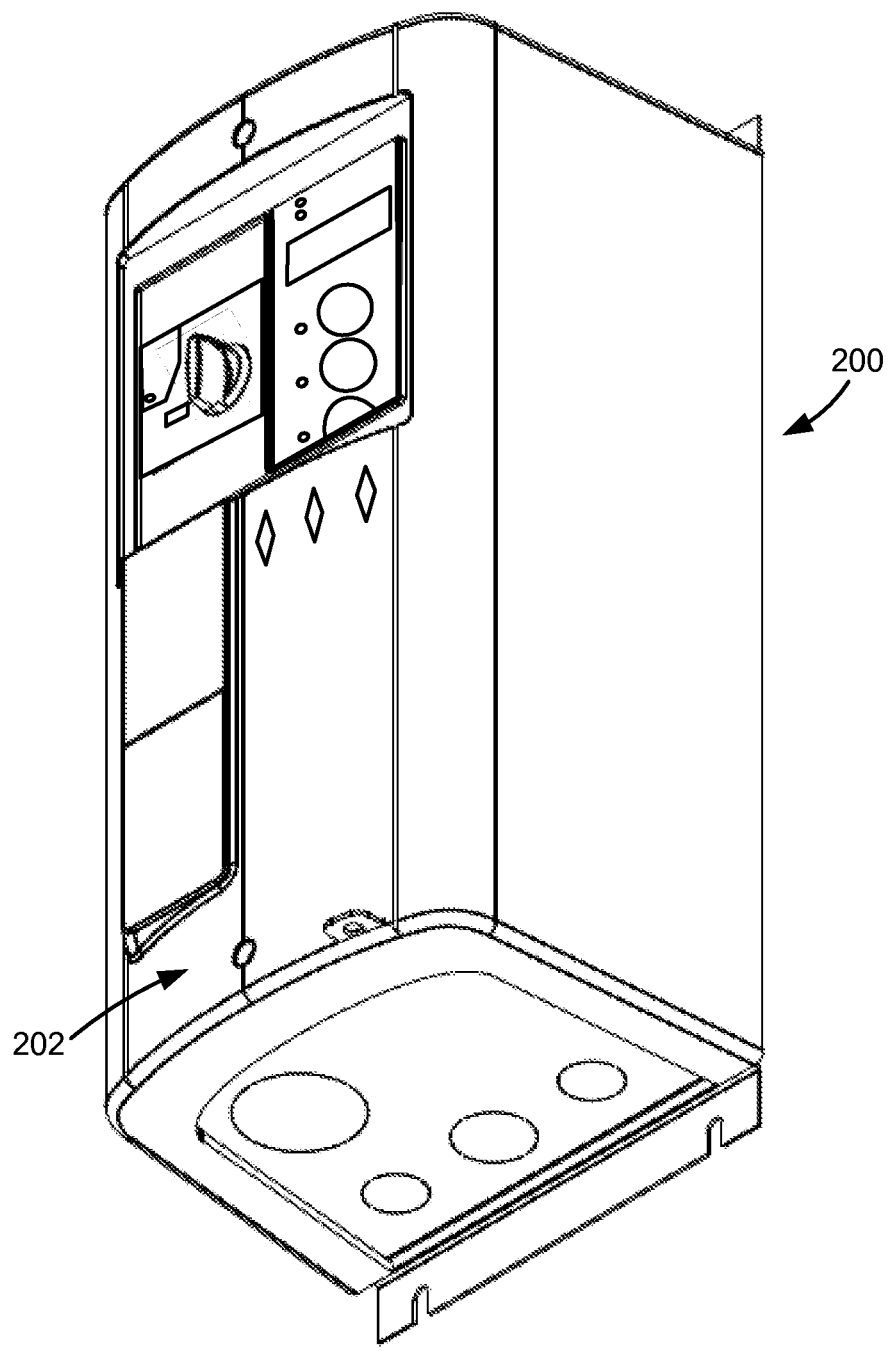
FIG. 2 illustrates a one embodiment of an enclosed motor starter.

FIG. 2 illustrates a one embodiment of an enclosed motor starter 200. FIG. 3 illustrates the motor starter 200 of FIG. 2 with the cover 202 removed to show the internal meter base 304, user interface 306, and control board assembly 308. FIG. 4 shows the meter base 304 of FIG. 3 removed from the starter 200. FIG. 3 also illustrates a contactor relay 310 and a start/disconnect switch 312. The meter base 304, independently illustrated in FIG. 4, also illustrates three integrated current transformers 314a, 314b, & 314c, which can help provide improved motor protection and improved metering accuracy.

The actual circuits employed by various starter embodiments consistent with the present application, as well as the correspondingly enabled functionality, can be specifically tailored to the desired installation and/or environment in which the starter is intended to be employed, as well as the type, size, class, rating, and/or capacity (horsepower, etc.) of the motor the starter is intended to operate and protect. Present starters can be configured for operation for purposes of building automation, industrial automation, fan, pump, or other motor operation, and/or energy metering, monitoring, or display, among other purposes. Depending on the particular intended installation/operating purpose, one or more specific advantageous features can be enabled by providing the corresponding starter control and/or protection circuitry.

As an example of illustrative potential features, provided merely for purposes of discussion, and not by way of limitation, starter features consistent with the present application can include integrated damper control; comprehensive metering with pulse/analog output enabled for enhanced data stream options; proof of flow status annunciation/indications to detect and identify belt loss, enhance comfort, and help protect equipment; BACnet or other protocol compatibility for substantially comprehensive energy monitoring and control (e.g., kW, kWh, etc.); enhanced controls compatibility to facilitate installation and improve interoperability; enhanced electronic motor protection by accommodating wide-ranging protection parameters and beneficial motor cycling protection; fireman's override input to purge smoke; and wide-range electronic overload relays to help reduce callbacks due to incorrectly sized overload relays being employed.

Figure 5A:
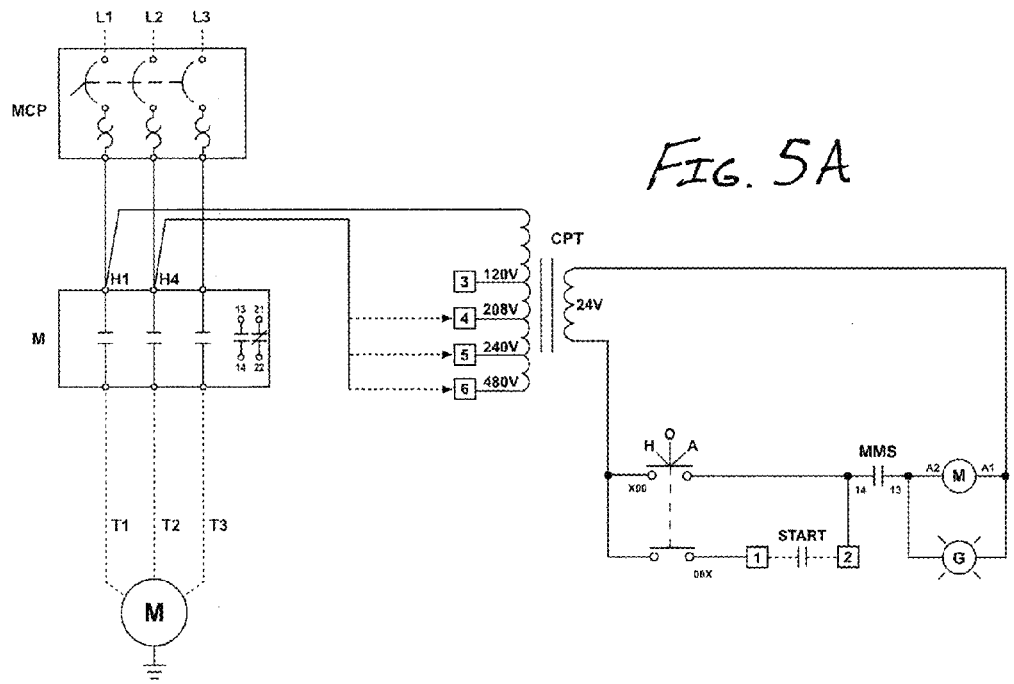
FIG. 5A schematically illustrates a wiring diagram for a starter embodiment particularly suited for operation in an automation system.
Figure 5B:
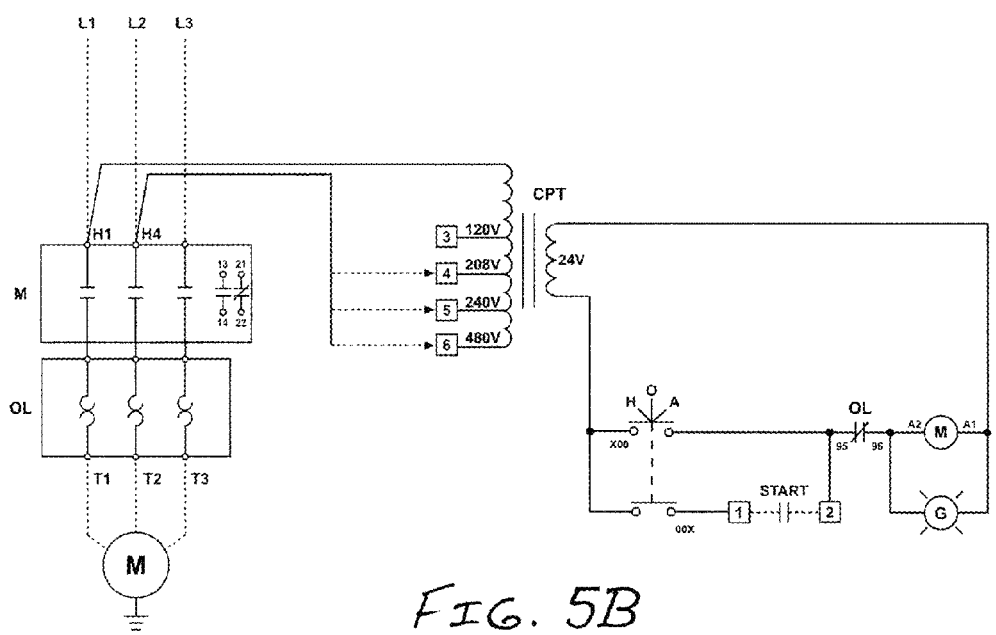
Figure 6A:
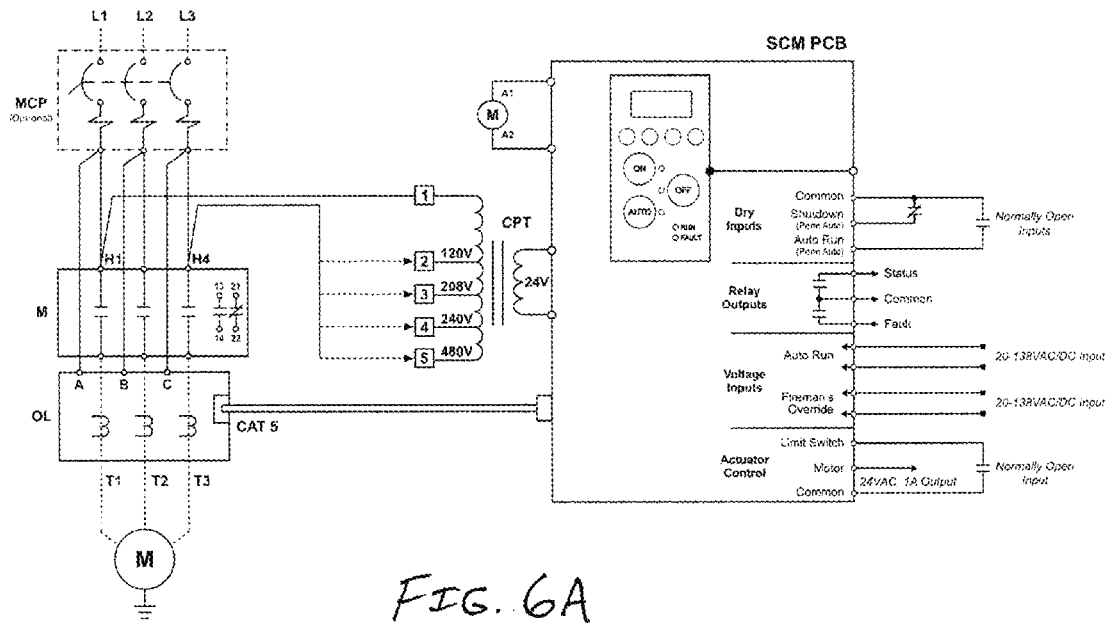
FIG. 6A schematically illustrates a wiring diagram for a starter embodiment particularly suited for operation in an automation system providing energy management functionality.
Figure 7:
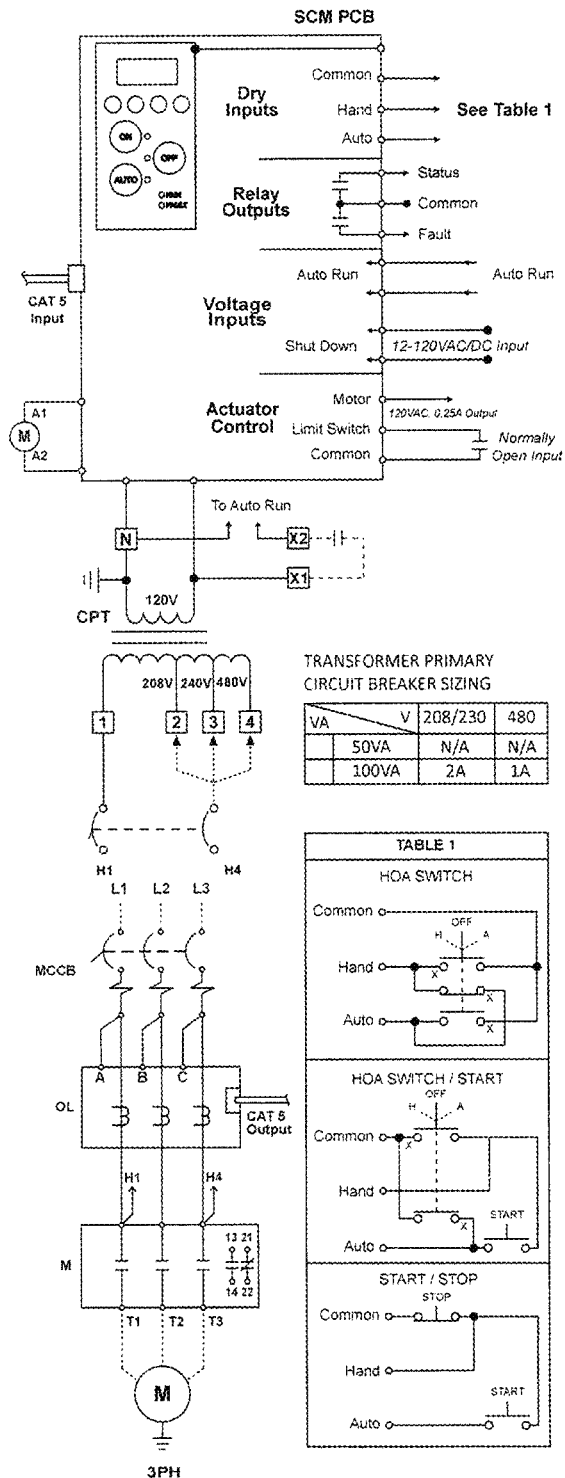
FIG. 7 schematically illustrates a wiring diagram for a starter embodiment particularly suited for operation in an automation system for pump operation and control.
Figure 8:
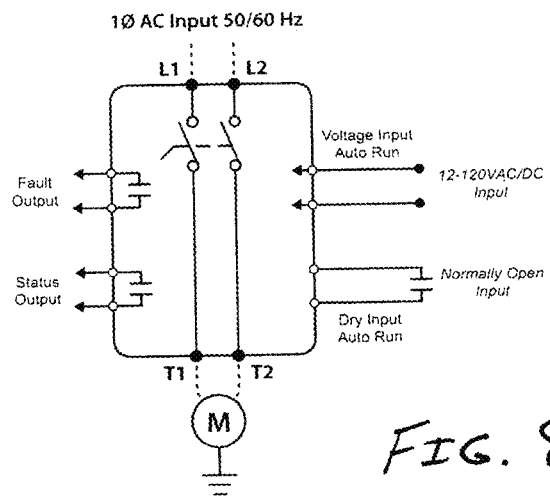
FIG. 8 schematically illustrates a wiring diagram for a starter embodiment particularly suited for operation of a relatively smaller, single-phase motor.
Figure 9A:
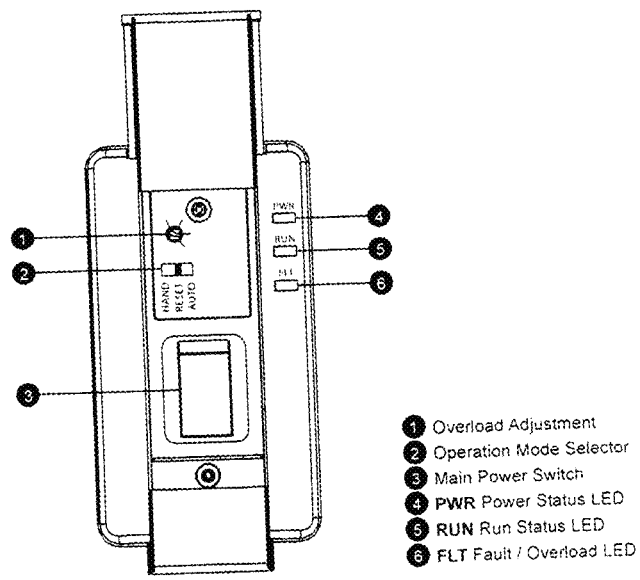
FIGS. 9A-9O illustrate alternative views, functions, and configurations of a starter such as one employing the schematically illustrated wiring diagram of FIG. 8.
Figures 9B, 9C:
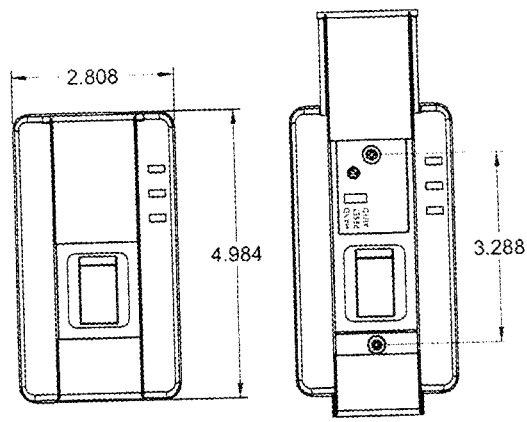
Figures 9D, 9E:
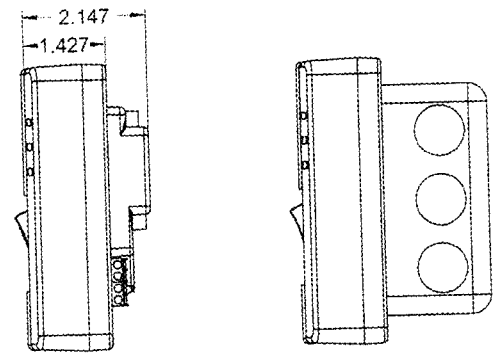
Figure 9F:
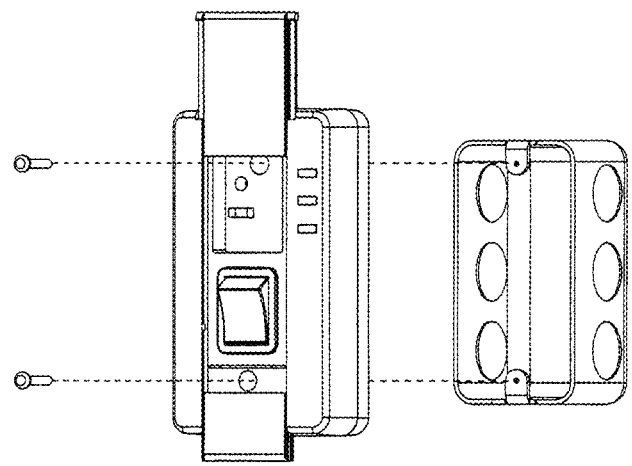
Figure 9G:
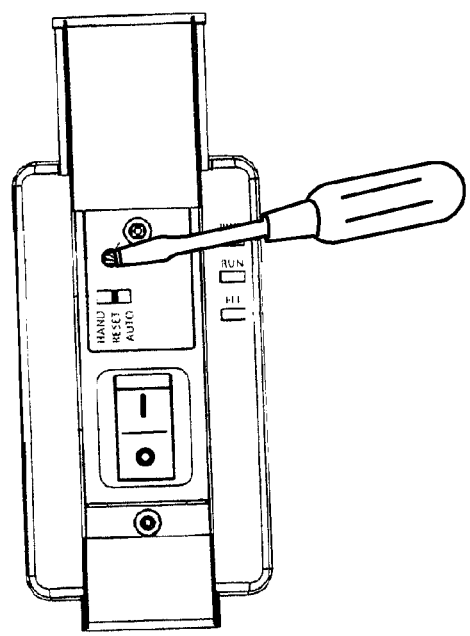
Figure 9H:
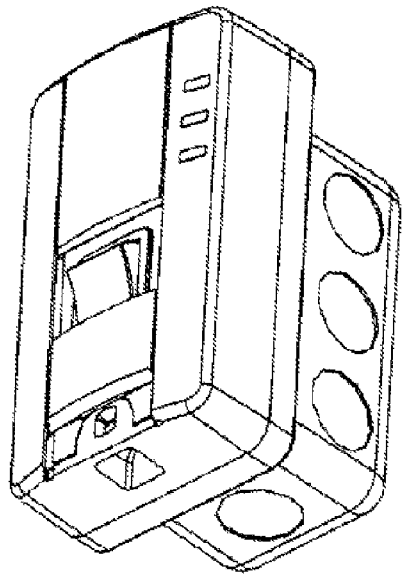
Figure 9I:
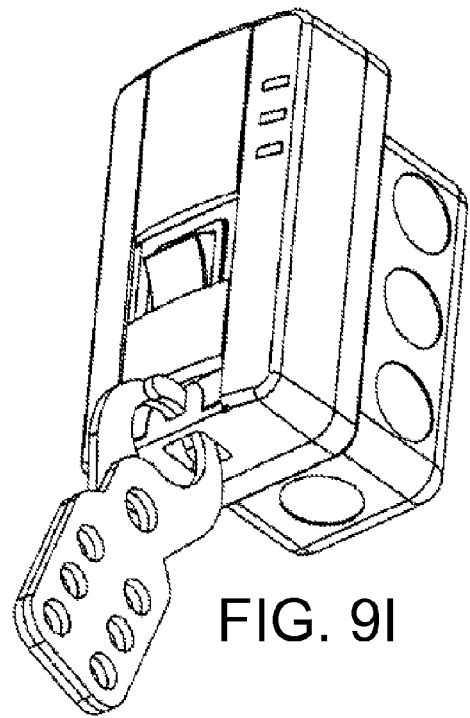
Figure 9J:
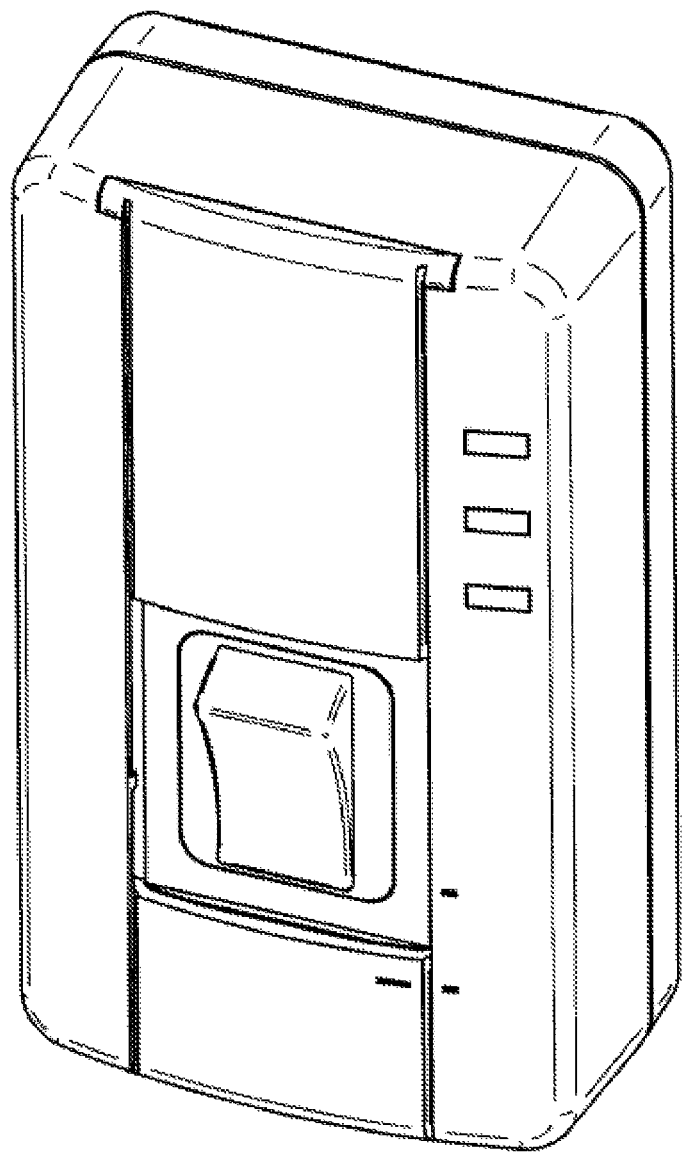
Figure 9K:
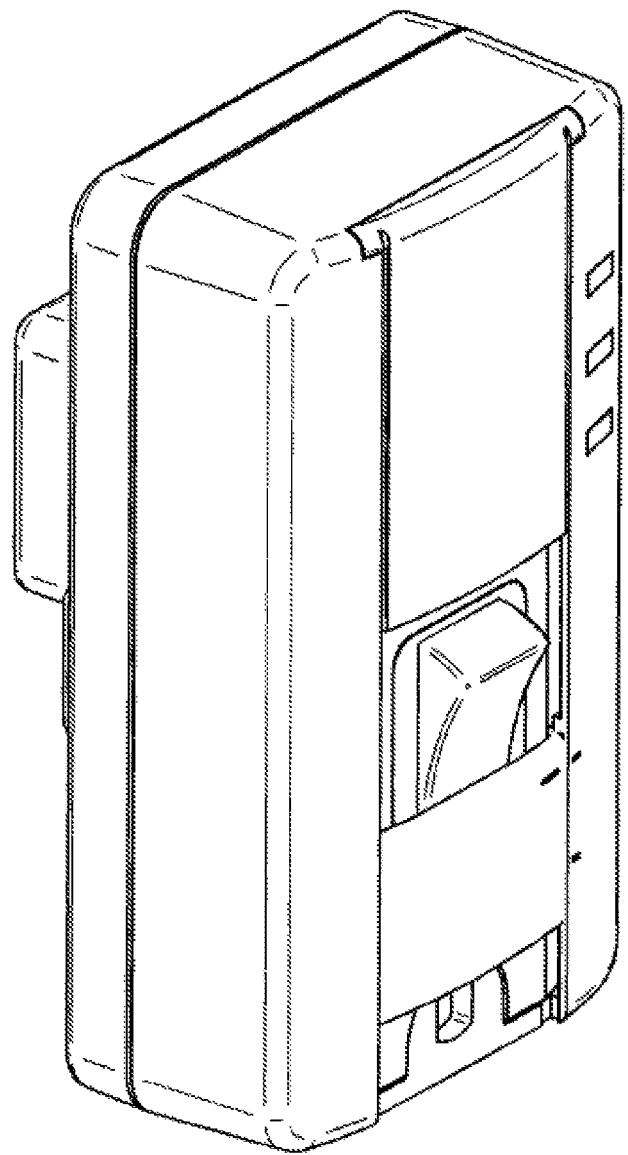
Figure 9L:
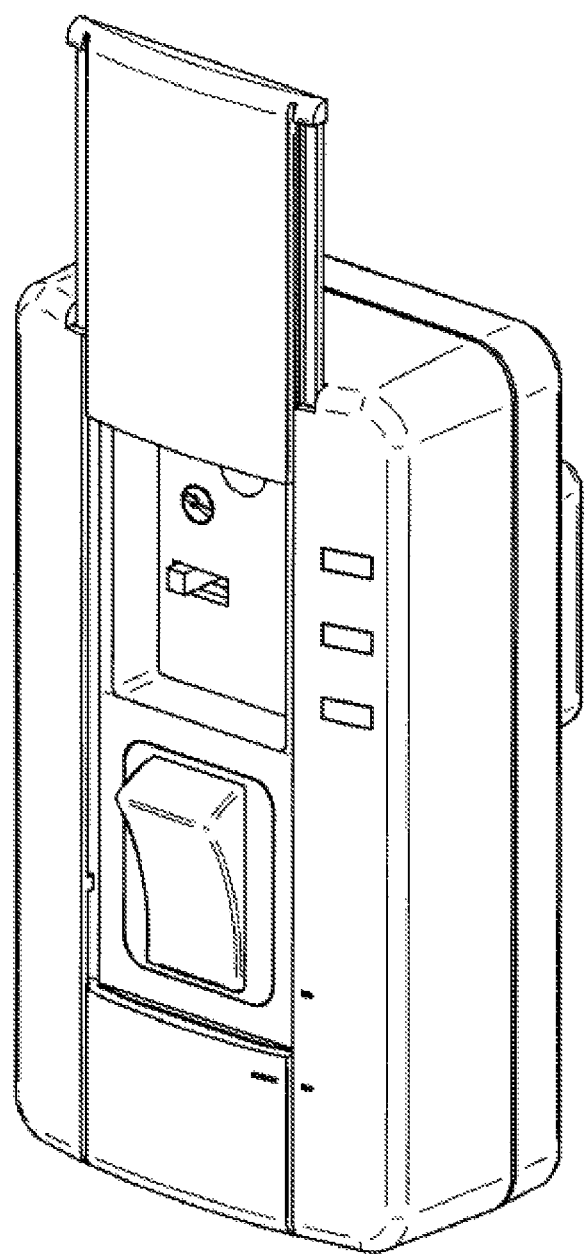
Figure 9M:
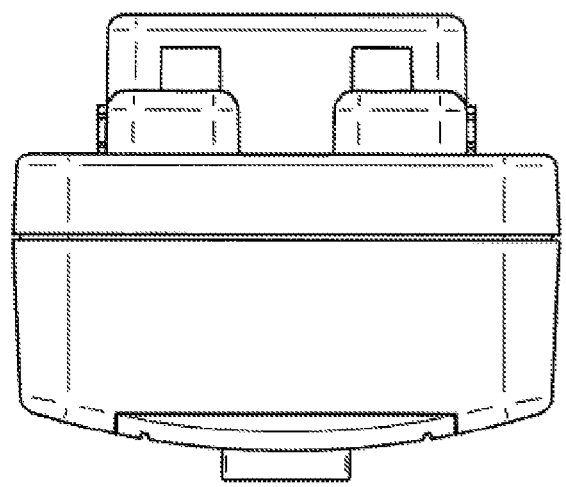
Figures 9N, 9O:
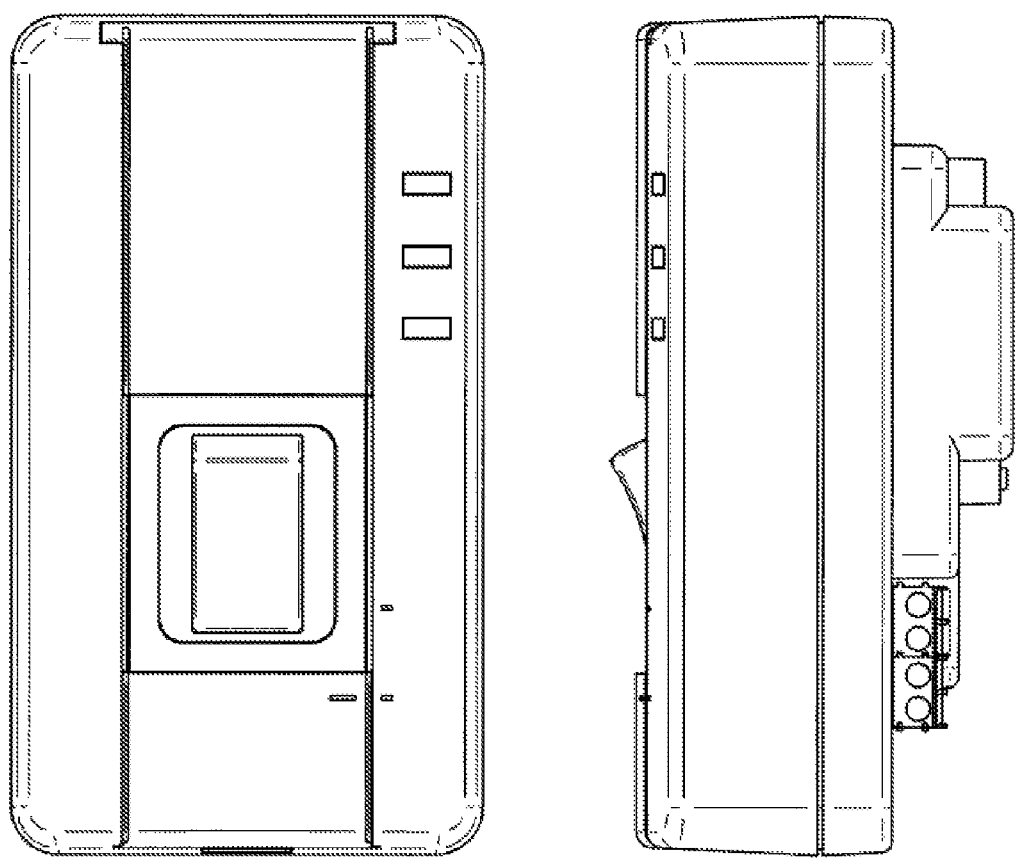

As an example of one starter embodiment, FIG. 5A schematically illustrates a wiring diagram for a starter embodiment particularly suited for operation in an automation system. FIGS. 5B-5C schematically illustrate alternative embodiments of the schematically illustrated wiring diagram of FIG. 5A. FIG. 6A schematically illustrates a wiring diagram for a starter embodiment particularly suited for operation in an automation system providing energy management functionality. FIGS. 6B-6C schematically illustrate alternative embodiments of the schematically illustrated wiring diagram of FIG. 6A. FIG. 7 schematically illustrates a wiring diagram for a starter embodiment particularly suited for operation in an automation system for pump operation and control. Alternatively, FIG. 8 schematically illustrates a wiring diagram for a starter embodiment particularly suited for operation of a relatively smaller, single-phase motor. FIGS. 9A-9O illustrate alternative views, functions, and configurations of a starter such as one employing the schematically illustrated wiring diagram of FIG. 8. Such a starter embodiment as illustrated in FIGS. 9A-9O, and employing the wiring diagram of FIG. 8, can accept a contact closure from standalone sensing devices such as carbon monoxide sensors or accept control signals from motion sensors and other peripheral sensors.

Figure 10:
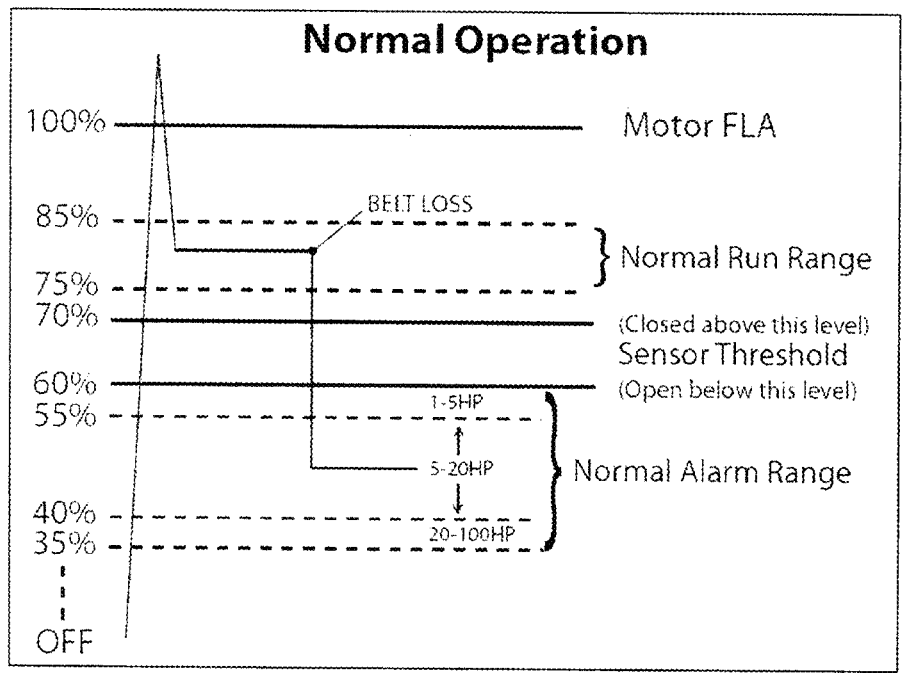
FIG. 10 graphically illustrates the effect of operating assumptions on a normally operated motor, consistent with the present subject matter.
Figure 11:
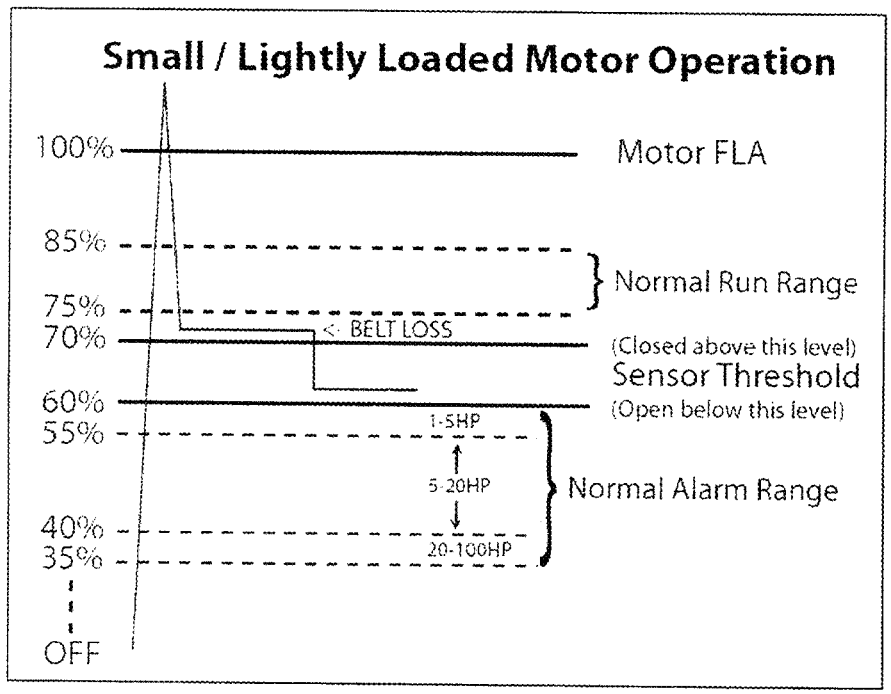
FIG. 11 graphically illustrates the effect of operating assumptions on a small or lightly loaded motor, consistent with the present subject matter.

FIG. 10 graphically illustrates the effect of operating assumptions on a normally operated motor, consistent with the present subject matter, and FIG. 11 graphically illustrates the effect of operating assumptions on a small or lightly loaded motor, consistent with the present subject matter.

For a proof-of-flow application and/or status annunciation, a current transformer, circuit measuring the current in shunt, or other current, voltage, or power characteristic sensing/calculating circuitry can be pre-configured to employ a trip point that is sufficiently and appropriately below the amperage represented by the indicated, expected, and or calculated full load amperage. For example, in proof of flow monitoring, a sensed motor current loss of approximately between 20-35% can be commonly experienced in response to a loss of load (e.g. belt break/loss, coupling shear, and/or other mechanical failure). In certain applications, a loss of up to 40% or more can be experienced (e.g., if you have a belt brake on a fan, as but one example). Examples of these types of relationships are graphically illustrated in FIG. 10 and FIG. 11.

Of course, those skilled in the art will appreciate that alternative applications can potentially result in other expected loss levels. A present monitoring circuit embodiment, being used for proof of flow, can be internally scaled so that for a given set point, it will employ a corresponding trip point that is proportionally and appropriately less than the provided set point. The quantity of offset can be predetermined and pre-configured into the current sensor at a given quantity below the full load amperage ("FLA") set point, such as 30% or 40%, as but two examples. Such an embodiment can offer a simple, convenient, and easy to use current sensors or other electronic circuit elements that can be pre-scaled, in an application specific way/amount, for proof of flow. Generally speaking, for most typical installations/environments, it is desirable to employ a trip point that is set far enough below FLA to avoid experiencing nuisance alarms and/or undue quantities of false trips, but close enough to FLA to detect, rapidly and accurately, anticipated possible loss of flow occurrences. It should be appreciated, however, that additional and/or alternative embodiments could employ different scaling methodologies, pre-established and/or field-configurable, for other applications, other types of monitoring, or other desired functionality. Similarly, alternative internal scaling could be preconfigured into circuit monitoring components used for alternative purposes/applications. However, those skilled in the art will readily appreciate that employing methodologies such as indicated above can allow for a starter embodiment to receive, detect, calculate, and/or otherwise determine the FLA value for the controlled and/or protected motor, and then provide proof-of-flow status, via the status relay outputs of starter embodiments such as those illustrated in FIGS. 5A-8, with such proof of flow status being monitored at an appropriately offset value from the FLA.

It will be obvious to those having skill in the art that many changes may be made to the details of the above-described embodiments without departing from the underlying principles of the invention. The scope of the present invention should, therefore, be determined only by the following claims.

The invention claimed is:

1. An apparatus for controllably providing operating power to a load, comprising:
   a control board assembly configured to receive an input and provide an output based, at least in part, on an operating mode selected by a user;
   a user interface allowing the user to select the operating mode for the control board assembly; and
   an electronic overload relay electronically interconnected with the control board assembly and a contactor relay, the contactor relay being selectively capable of supplying operating power to a load;
   wherein, upon the control board assembly receiving a start input:
   the contactor relay is enabled to supply operating power to the load;
   the electronic overload relay senses one or more aspects of the operating power supplied to the load; and
   based at least in part on the sensed one or more aspects of the operating power, the control board assembly operates a status relay outputting an indication of operating status of the load, wherein the indication of operating status of the load indicates proof of flow.

2. The apparatus of claim 1, wherein the sensed one or more aspects of the operating power includes a sensed voltage and a sensed current.

3. The apparatus of claim 2, wherein the sensed voltage and the sensed current are used to calculate true power of the load.

4. The apparatus of claim 1, wherein the sensed one or more aspects of the operating power includes a sensed current.

5. The apparatus of claim 4, wherein the current is measured in shunt.

6. The apparatus of claim 1, wherein the control power is single phase power.

7. The apparatus of claim 1, wherein the control power is three phase power.

8. The apparatus of claim 1, further comprising a manual control enabling the user to select the operating mode.

9. The apparatus of claim 8, wherein the manual control is a keypad having one or more manual switches.

10. The apparatus of claim 9, wherein the one or more manual switches allow the user to select an operating mode from among the following: hand/manual, auto, and off.

11. The apparatus of claim 1, wherein the status relay outputs the indication of operating status when a sensed running current for the load is within a predetermined acceptable range.

12. The apparatus of claim 1, wherein the status relay outputs the indication of operating status when a sensed running current for the load is at least a predetermined percentage of a full load amperage for the load.

13. The apparatus of claim 12, wherein the full load amperage is indicated by the user through the user interface.

14. The apparatus of claim 1, wherein the control board assembly further includes a relay enabling integrated damper control.

15. The apparatus of claim 1, wherein the control board is configured to receive the start input manually or from a remote automation source.

16. The apparatus of claim 1, wherein the control board is configured to accept a fireman's override input.

17. The apparatus of claim 1, wherein the control board and electronic overload relay cooperatively enable power metering for the load.

18. The apparatus of claim 1, further comprising a power circuit enabling the control board to function off of alternate operating power levels.

19. The apparatus of claim 18, wherein the power circuit includes a multi-tap control power transformer.

20. The apparatus of claim 1, wherein the control board assembly, the user interface, the electronic overload relay, and the contactor relay are all provisioned within a single enclosure and interconnected so as to encompass a starter apparatus.

21. The apparatus of claim 20 further comprising a load disconnect circuit integrated within the enclosure so as to encompass a combination starter.

22. The apparatus of claim 20, wherein the enclosure is configured to provide lockout functionality.

23. The apparatus of claim 1, wherein the overload relay, the control board assembly, and the user interface are provisioned within a single enclosure, and the enclosure further includes a repositionable member.

24. The apparatus of claim 23, wherein the repositionable member alternates between a first position and a second position, wherein, in the first position the repositionable member exposes at least a portion of the user interface, and in the second position the repositionable member conceals the at least a portion of the user interface.

25. The apparatus of claim 24 wherein the repositionable member at least partially enables a lockout feature.

26. An apparatus for controllably providing operating power to a load, comprising:
a control board assembly including a relay enabling integrated damper control, and configured to receive an input and provide an output based, at least in part, on an operating mode selected by a user;
a user interface allowing the user to select the operating mode for the control board assembly; and
an electronic overload relay electronically interconnected with the control board assembly and a contactor relay, the contactor relay being selectively capable of supplying operating power to a load;
wherein, upon the control board assembly receiving a start input:
the contactor relay is enabled to supply operating power to the load;
the electronic overload relay senses one or more aspects of the operating power supplied to the load; and
based at least in part on the sensed one or more aspects of the operating power, the control board assembly operates a status relay outputting an indication of operating status of the load.

27. An apparatus for controllably providing operating power to a load, comprising:
a control board assembly configured to receive an input and provide an output based, at least in part, on an operating mode selected by a user, and further configured to accept a fireman's override input;
a user interface allowing the user to select the operating mode for the control board assembly; and
an electronic overload relay electronically interconnected with the control board assembly and a contactor relay, the contactor relay being selectively capable of supplying operating power to a load;
wherein, upon the control board assembly receiving a start input:
the contactor relay is enabled to supply operating power to the load;
the electronic overload relay senses one or more aspects of the operating power supplied to the load; and
based at least in part on the sensed one or more aspects of the operating power, the control board assembly operates a status relay outputting an indication of operating status of the load.

28. A method for providing power to a load, the method comprising the steps of:
electronically interconnecting an electronic overload relay with a control board assembly and a contactor relay, the contactor relay being selectively capable of supplying operating power to a load, and the control board assembly configured to receive an input and provide an output based, at least in part, on an operating mode selected by a user;
providing a user interface allowing the user to select the operating mode for the control board assembly; and
configuring the control board assembly to receive a start input, and upon the control board assembly receiving the start input:
the contactor relay is enabled to supply operating power to the load;
the electronic overload relay senses one or more aspects of the operating power supplied to the load; and
based at least in part on the sensed one or more aspects of the operating power, the control board assembly operates a status relay outputting an indication of operating status of the load, wherein the indication of operating status of the load indicates proof of flow.

29. The method of claim 28, wherein the one or more aspects of the operating power sensed by the electronic overload relay are chosen from among a sensed voltage and a sensed current.

30. The method of claim 28, wherein the status relay outputs the indication of operating status of the load when a sensed running current for the load is at least predetermined percentage of a full load amperage for the load.

31. The method of claim 30, wherein the contractor relay is enabled to disconnect operating power to the load when a second sensed running current for the load is less than a second predetermined percentage of the full load amperage for the load.

32. The method of claim 30, wherein the full load amperage for the load is input through the user interface.

33. The method of claim 28, wherein control board assembly enables integrated damper control through an included relay.

34. The method of claim 28, wherein the control board assembly accepts a fireman's override input.

* * * * *